US010809187B2

(12) United States Patent
Eikje

(10) Patent No.: US 10,809,187 B2
(45) Date of Patent: Oct. 20, 2020

(54) ANALYTICAL METHOD FOR COMMON AND SPECIFIC CHARACTERIZATION OF SKIN CARCINOGENESIS BY FTIR MICROSPECTROSCOPY

(71) Applicants: MC Professional OU, Tallinn (EE); Irina Skrebova, Tallinn (EE); Natalja Eikje, Tysvaervaag (NO)

(72) Inventor: Natalja Eikje, Tysvaervaag (NO)

( * ) Notice: Subject to any disclaimer, the term of this patent is extended or adjusted under 35 U.S.C. 154(b) by 365 days.

(21) Appl. No.: 14/378,120

(22) PCT Filed: Feb. 21, 2013

(86) PCT No.: PCT/EE2013/000001
§ 371 (c)(1),
(2) Date: Apr. 22, 2019

(87) PCT Pub. No.: WO2013/123950
PCT Pub. Date: Aug. 29, 2013

(65) Prior Publication Data
US 2019/0317015 A1 Oct. 17, 2019

Related U.S. Application Data

(60) Provisional application No. 61/595,050, filed on Feb. 21, 2012.

(51) Int. Cl.
| G01N 21/3563 | (2014.01) |
| G01N 33/574 | (2006.01) |
| C12Q 1/6886 | (2018.01) |
| G01N 21/956 | (2006.01) |
| G06F 17/18 | (2006.01) |
| G01N 21/35 | (2014.01) |

(52) U.S. Cl.
CPC ....... *G01N 21/3563* (2013.01); *C12Q 1/6886* (2013.01); *G01N 21/95607* (2013.01); *G01N 33/574* (2013.01); *G06F 17/18* (2013.01); *G01N 2021/3595* (2013.01)

(58) Field of Classification Search
CPC ............... G01N 21/35; G01N 21/3563; G01N 33/4833; G01N 2021/3595; G01N 33/574; A61B 5/0075; C12Q 1/6886
See application file for complete search history.

(56) References Cited

U.S. PATENT DOCUMENTS

| 5,539,207 | A | 7/1996 | Wong | |
| 6,031,232 | A | 2/2000 | Cohenford et al. | |
| 2012/0259229 | A1* | 10/2012 | Wang | G01N 21/65 600/476 |
| 2014/0058224 | A1* | 2/2014 | Gellermann | G01N 21/65 600/314 |

FOREIGN PATENT DOCUMENTS

| AU | 2013224476 B2 | 2/2017 |
| CA | 2901954 A1 | 8/2013 |
| JP | 2015508166 A5 | 7/2017 |
| WO | 2010067353 A3 | 11/2010 |
| WO | 2013123950 A4 | 10/2013 |

OTHER PUBLICATIONS

Eikje Natalja Skrebova ED—Kollias Nikiforos et al: "DNA-RNA, DNA-DNA, DNA-protein and protein-protein interactions in diagnosis of skin cancers by FT-IR micro spectroscopy", Photon IC Therapeutics and Diagnostics VII, SPIE, 1000 20th St. Bellingham WA 98225-6705 USA, vol. 7883, No. 1, Feb. 10, 2011 (Feb. 10, 2011), pp. 1-5, XP060006072.
Eikje N S: "Numerical modeling and analytical treatment of IR spectra in the diagnosis of skin cancers", Proceedings of SPIE, SPIE—International Society for Optical Engineering, Bellingham, WA, US, vol. 7999, Oct. 22, 2010 (Oct. 22, 2010), pp. 1-6, XP002698177.
Eikje N S: "Vibrational spectroscopy for molecular characterisation and diagnosis of benign, premalignant and malignant skin tumours", Biotechnology Annual Review, vol. 11, ISSN: 1387-2656, Oct. 7, 2005 (Oct. 7, 2005), pp. 191-226.
Natalja Skrebova Eikje: "Potential of lasers and optical technologies for clinical applications in dermatology /title", Proceedings of SPIE, vol. 6163, Aug. 1, 2006 (Aug. 1, 2006), pp. 616309-616309-16, XP55067 434.
Federman, D.G.; Concato, J.; Kirsner, R.S., "Screening for skin cancer: absence of evidence", Arch. Dermatol., (2009), vol. 145, p. 926.
Digiovanni, J., "Multistage carcinogenesis in mouse skin", Pharmacol. Ther., (1992), vol. 54, No. 1, pp. 63-128.
Chimento, S.M.; Kirsner, R.S., "Understanding the role of c-Jun and Jun B transcription factors in skin cancer development", J. Invest. Dennatol., (2011), vol. 131, p. 1002.
WIPO, International Search Report for PCT international patent application serial No. PCT/EE2013/00001, dated Jun. 18, 2013, 4 pages.
WIPO, International Preliminary Report on Patentability Chapter I for PCT international patent application serial No. PCT/EE2013/00001, including the Written Opinion of the International Searching Authority, dated Aug. 26, 2014, 8 pages.

(Continued)

*Primary Examiner* — David P Porta
*Assistant Examiner* — Fani Boosalis
(74) *Attorney, Agent, or Firm* — D'Hue Law LLC; Cedric A. D'Hue

(57) ABSTRACT

The invention presents methods of using Fourier transform infrared (FTIR) microspectroscopy for common and specific characterization of carcinogenesis in human skin tumors. The invention provides the user with the method to analyse intra- and inter-molecular interactions for nucleic acids and proteins expressed in infrared (IR) spectra of human skin epidermal cancers towards understanding the molecular, cellular and tissue changes that occur during skin carcinogenesis. More particularly, presented analytical method has the advantage to simultaneously observe DNA-RNA, DNA-DNA, DNA-protein and protein-protein interactions by means of their expressed interacting activity levels within one type of tumour and between different types of tumours, both commonly and specifically, with further indication of the grade of activity in benign, premalignant and malignant skin tissue cells.

21 Claims, No Drawings

(56) References Cited

OTHER PUBLICATIONS

IP Australia, Notice of Acceptance for Australian patent application serial No. 2013224476, dated Jan. 17, 2017, 4 pages.
IP Australia, PCT Amendments for Australian patent application serial No. 2013224476, dated Sep. 19, 2014, 13 pages.
IP Australia, Examination Report No. 1 for Australian patent application serial No. 2013224476, dated Jan. 29, 2016, 3 pages.
IP Australia, Amendment for Australian patent application serial No. 2013224476, dated Oct. 17, 2016, 10 pages.
IP Australia, Amendment for Australian patent application serial No. 2013224476, dated Oct. 17, 2016, 25 pages.
IP Australia, Amendment for Australian patent application serial No. 2013224476, dated Oct. 17, 2016, 37 pages.
IP Australia, Amendment for Australian patent application serial No. 2013224476, dated Oct. 17, 2016, 31 pages.
IP Australia, Examination Report No. 2 for Australian patent application serial No. 2013224476, dated Nov. 18, 2016, 3 pages.
IP Australia, Amendment for Australian patent application serial No. 2013224476, dated Dec. 8, 2016, 1 page.
IP Australia, Amendment for Australian patent application serial No. 2013224476, dated Dec. 8, 2016, 5 pages.
IP Australia, Amendment for Australian patent application serial No. 2013224476, dated Dec. 8, 2016, 23 pages.
IP Australia, Amendment for Australian patent application serial No. 2013224476, dated Dec. 8, 2016, 35 pages.
IP Australia, Voluntary Amendment for Australian patent application serial No. 2013224476, dated May 30, 2017, 3 pages.
IP Australia, Voluntary Amendment for Australian patent application serial No. 2013224476, dated May 30, 2017, 5 pages.
IP Australia, Voluntary Amendment for Australian patent application serial No. 2013224476, dated May 30, 2017, 17 pages.
IP Australia, Voluntary Amendment for Australian patent application serial No. 2013224476, dated May 30, 2017, 19 pages.
IP Australia, Voluntary Amendment for Australian patent application serial No. 2013224476, dated May 30, 2017, 41 pages.
IP Australia, Voluntary Amendment for Australian patent application serial No. 2013224476, dated May 30, 2017, 42 pages.
IP Australia, Examination Report on Voluntary Amendments for Australian patent application serial No. 2013224476, dated Jun. 30, 2017, 3 pages.
WIPO, Written Opinion of the International Searching Authority for PCT international patent application serial No. PCT/EE2013/00001, dated Jun. 18, 2013, 7 pages.
Israel Patent Office, Notice of Defects in Patent Application for Israel patent application serial No. 234048, dated Apr. 24, 2017, 3 pages.
Israel Patent Office, English Translation of Notice of Defects in Patent Application for Israel patent application serial No. 234048, dated Apr. 24, 2017, 3 pages.
Applicant, Response to Notice of Defects in Patent Application for Israel patent application serial No. 234048, dated Jul. 6, 2018, 6 pages.

* cited by examiner

ANALYTICAL METHOD FOR COMMON AND SPECIFIC CHARACTERIZATION OF SKIN CARCINOGENESIS BY FTIR MICROSPECTROSCOPY

BACKGROUND OF THE INVENTION

1. Field of the Invention

The present invention is directed towards providing an optical method for non-destructive characterization of carcinogenesis in skin cancerous tissues based on Fourier transform infrared (FTIR) microspectroscopy. More specifically, the invention provides with an analytical method for simultaneous observation and further characterization of intra- and inter-molecular interactions for nucleic acids and proteins, commonly and specifically expressed in IR spectra of each type of pathology, that also finds use for indication of the grade of neoplastic activity in cells in human skin cancerous tissues.

2. Prior Art

Publications and other reference materials referred to herein, including reference cited therein, are incorporated herein by reference in their entirety and are numerically referenced in the following text and respectively grouped in the appended Bibliography, which immediately preceds the claims.

In many countries skin cancer affects more people than all other cancers combined [1], but there is not yet enough understanding about the molecular, cellular and tissue changes that occur during skin carcinogenesis, that will have impact on clinical diagnosis, monitoring and treatment of skin cancer.

For many years the mouse skin model provided a possibility to study multistage carcinogenesis mechanisms [2], but without direct relevance of this model system to human skin cancers.

Up-to-date literature describes skin cancer development is, in part, under genetic control, and transcription factors (TFs), which are sequence-specific DNA-binding proteins, that control transcriptional activation or regression and thus control cell growth, being important in this process [3].

However, existing methods do not permit studying mechanisms of cancerogenesis directly on human beings and do not answer to all existing questions at present.

For better understanding of molecular and cellular mechanisms involved in skin cancer development, there is a need for a method to directly characterize carcinogenesis from hyperplasia to invasive cancer, from one type of cancer to another type of cancer, from one patient to the group of patients with the same pathology.

Skin tissue IR microspectroscopy technique is a tool for spectroscopic evaluation of unstained tissue of skin biopsies. It is an objective method for the analysis of skin tissue section that uses the chemical composition of the tissue as an indicator for healthy or pathological state of the cells in the tissue. IR spectral information objectively and quantitatively determines variations in the chemical composition of skin cells and tissue, that can be further "converted" to medical knowledge. It is a sensitive tool for studying isolated biomolecules alone and in interactions.

Feasibility of application of IR microspectroscopy for spectral characterization of the most common skin precancers and cancers has been already introduced in the 900-1700 cm-1 region, revealing the most visible changes related to protein conformation and nucleic acid bases, that in general showed modifications and enhancement with progression to malignancy in that region [4].

Detailed alignment of the peaks for nucleic acids and proteins with spectral variations in IR spectra from skin epidermal cancers described appearance of DNA peak at about 965 cm-1; the multiplet (DNA/RNA) at about 1055 cm-1; DNA/RNA triad peaks at about 1071, 1084/1085, 1095 cm-1; at about 1245 cm-1 as a combination for DNA and amide III; a number of non-specific (non-descriptive) proteins at about 1310, 1390 and 1450 cm-1; the amide II vibration at about 1540 cm-1; and the amide I vibration at about 1650 cm-1 [5]. Nevertheless, the problem has not been yet addressed towards common and specific characterization of carcinogenesis in human skin tumours by FTIR microspectroscopy.

Therefore, it is another purpose of this invention to provide an optical analytical method for objective evaluation of intra- and inter-molecular interactions for nucleic acids and proteins expressed in infrared (IR) spectra of epidermal skin cancers towards understanding the molecular, cellular and tissue changes that occur during skin carcinogenesis.

SUMMARY OF THE INVENTION

In a first aspect, the invention provides a method of using FTIR microspectroscopy for characterization of common and specific carcinogenesis in human biopsied cancerous tissue samples. The sample can be comprised of normal, benign, precancerous or cancerous cells on a tissue sample. The invented method is based on simultaneous characterization of intra- and inter-molecular interactions for nucleic acids and proteins by means of their expressed interacting activity levels in infrared (IR) spectra of benign, premalignant and malignant skin cancers, in comparison to IR spectra from healthy, i.e. normal/unchanged, skin tissue. More particularly, provided method allows to describe common and specific features of skin carcinogenesis for each type of cancer and between different types of cancers, to assess the activity of neoplastic cells in each patient and between the patients by FTIR microspectroscopy.

Skin epidermal carcinogenesis is a multi-stage process, that involves at least 3 mechanistically distinct steps—initiation, promotion and progression. Skin cancer generally develops in the epidermis. Most common malignant skin cancers are basal cell carcinoma (BCC), squamous cell carcinoma (SCC) and malignant melanoma (MM), that have been used as examples for the user of invention. To further provide the user with the invention steps, Bowen's disease, has been chosen as an example of precancerous skin lesion, well-known as intraepidemnnal carcinoma in situ. Benign compound nevus has been chosen as a common example of benign skin tumour in the presented invention.

The method can be carried out manually and comprises the following steps:

i. obtaining FTIR spectra from a multitude of pathological sites on a sample to obtain a multitude of measurements for each sample ii. determining the specified wavenumber region between 900 and 1300 cm-1 for nucleic acids and the specified wavenumber region between 1300 and 1700 cm-1 for proteins in each measured IR spectrum iii. normalizing each of IR spectrum to amide I peak iv. averaging epidermal measurements to obtain an average spectrum for the sample In the above method, the biopsied tissue samples are prepared for measurements by using FTIR microspectroscopy by the following steps:

i. strictly sequential 2 sample cuts having a thickness of 6 micrometers ii. staining 1 sample cut with hematoxilin and eosin for histopathological evaluation iii. air-drying 1 sample cut on CaF2 slide glass for collection of FTIR spectra Although skin tissue is used throughout this description as the representative tissue, it should be understood that the invention method is not limited to measuring epidermal skin tissue and can be exploited with other tissues, as will be apparent to the skilled person.

All the above and other characteristics and advantages of the invention will be further described.

DETAILED DESCRIPTION OF THE INVENTION

The invention will now be further explained through description of preferred embodiments.

All the FTIR microscopy measurements were performed using a JEOL Co. (Tokyo, Japan) FT-IR spectrometer, a model IR-MAU200. Before each measurement, a calibration was performed using a sample provided with the instrument by the manufacturer and proper operating conditions of FTIR microspectrometer was confirmed.

The data used in the examples below is derived from tissue specimen from the biopsy archive of the Department of Dermatology, Tokushima University School of Medicine, Tokushima, Japan, and a courtesy of Dr. T. Ikehara from the Department of Orthopedics, Tokushima University School of Medicine, Tokushima, Japan.

The tissue samples used for FT-IR microspectroscopy were in the dry state, while the corresponding slides observed by light microscope were stained with hematoxilin and eosin for the identification of the tissue structure. The aperture size used in the measurements was 25 over 25 micrometers.

Initially, the background spectrum was collected. After the measurement site was chosen using the visible light, the microscope was changed to IR mode. The number of co-added scans were increased to 127 to achieve high signal to noise ratio. The measured spectra covered the wavenumber range between 800 and 4000 cm-1, at a resolution of 4 cm-1.

A database of having totally measured 198 spectra in the epidermis, both pathological and non-pathological, was created from 13 patients with malignant tumours: basal cell carcinoma (BCC) (6 patients), squamous cell carcinoma (SCC) (4 patients), malignant melanoma (MM) (3 patients); from 4 patients with benign tumours: benign compound nevus (4 patients); from 3 patients with precancers: Bowen's disease (3 patients); and from 4 healthy subjects.

The invention method included the following steps for determination of the activity levels for nucleic acids and proteins in the IR spectra of BCC, SCC, MM, Bowen's disease and benign compound nevus, in comparison to IR spectra from healthy subjects:

calculation of mean values of each determined nucleic acids peaks calculation of mean values of each determined protein (specific and non-specific) peak a comparison of the intensities of all determined nucleic acids peaks in the 900-1300 cm-1 region with the intensity of the peak at about 1245 cm$^{-1}$ by calculating the following intensity peaks ratios: $I_{(965)}/I_{(1245)}$, $I_{(1055)}/I_{(1245)}$, $I_{(max\ peak\ among\ DNA/RNA\ triad\ peaks)}/I_{(1245)}$.

a comparison of the intensities of all determined peaks for specific and nonspecific proteins in the 1300-1700 cm$^{-1}$ region with the intensity of amide I peak at about 1650 cm$^{-1}$ by calculating the following peaks ratios: $I_{(1310)}/I_{(1650)}$, $I_{(1390)}/I_{(1650)}$, $I_{(1450)}/I_{(1650)}$, $I_{(1540)}/I_{(1650)}$.

a calculation of the level of activity of DNA-RNA vs. DNA-protein interactions by the following ratio: $I_{(sum\ mean\ DNA/RNA\ triad\ peaks)}/I_{(1245)}$.

a comparison of the level of activity of multiplet (DNA/RNA) with the level(s) of activity of the peaks in DNA/RNA triad.

Below is a summary of the data employed from the patients with BCC, SCC, MM, Bowen's disease, benign compound nevus and healthy subjects, provided in examples.

Intra- and Inter-Molecular Interactions for Nucleic Acids

EXAMPLES

Example 1

BCC

Spectral data epidermally measured from 6 patients with BCC on nucleic acids peaks mean values (965 cm$_{-1}$, 1055 cm$_{-1}$, the most prominent peak in DNA/RNA triad peaks), the intensity ratios and proportional ratios (sum mean DNA/RNA triad peaks vs. 1245 cm$_{-1}$).

2 BCC patterns in 6 patients, based on expressed mean values vs. proportional ratios:

965mean<1055mean<DNA/RNA triad max peak mean

965mean<1055mean>DNA/RNA triad max peak mean

| | | |
|---|---|---|
| 1) 0.35 < 0.44 < 0.45 | vs. | [1:1] |
| 2) 0.31 < 0.43 < 0.48 | vs. | [1:1] |
| 3) 0.35 < 0.42 > 0.40 | vs. | [1:1] |
| 4) 0.11 < 0.19 > 0.18 | vs. | [0.8:1] |
| 5) 0.08 < 0.14 < 0.16 | vs. | [0.8:1] |
| 6) 0.09 = 0.09 < 0.23 | vs. | [0.8:1] |

1 BCC pattern in 6 patients, based on calculated intensity ratios vs. proportional ratios:

$I(965)/I(1245)<I(1055)/I(1245)<I(DNA/RNA$ triad max peak$)/I(1245)$ (independent on the grade of activity)

| | | |
|---|---|---|
| 1) 0.75 < 0.94 < 0.96 | vs. | [1:1] |
| 2) 0.71 < 0.98 < 1.09 | vs. | [1:1] |
| 3) 0.88 < 1.05 < 1.00 | vs. | [1:1] |
| 4) 0.50 < 0.87 < 0.82 | vs. | [0.8:1] |
| 5) 0.38 < 0.67 < 0.76 | vs. | [0.8:1] |
| 6) 0.45 < 0.45 < 1.15 | vs. | [0.8:1] |

Example 2

SCC

Spectral data epidermally measured from 4 patients with SCC on nucleic acids peaks mean values (965 cm$_{-1}$, 1055 cm-1, the most prominent peak in DNA/RNA triad peaks), the intensity ratios and proportional ratios (sum mean DNA/RNA triad peaks vs. 1245 cm-1).

3 SCC patterns in 4 patients, based on expressed mean values vs. proportional ratios:

965mean<1055mean>DNA/RNA triad max peak mean vs.[1:1]

965mean<105mean<DNA/RNA triad max peak mean vs.[0.9:1]

965mean>1055mean<DNA/RNA triad max peak mean vs.[0.7:1]

| | | |
|---|---|---|
| 1) 0.60 < 0.66 > 0.65 | vs. | [1:1] |
| 2) 0.26 < 0.30 < 0.35 | vs. | [0.9:1] |
| 3) 0.19 > 0.13 < 0.16 | vs. | [0.7:1] |
| 4) 0.07 > (—) < 0.12 | vs. | [0.7:1] |

2 SCC patterns in 4 patients, based on calculated intensity ratios vs. proportional ratios:

$I(965)/I(1245)<I(1055)/I(1245)>I$(DNA/RNA triad max peak)$/I(1245)$ (for high activity levels of the peak at about 1055 cm-1)

$I(965)/I(1245)>I(1055)/I(1245)<I$(DNA/RNA triad max peak)$/I(1245)$ (for low activity levels of the peak at about 1055 cm-1)

| | | |
|---|---|---|
| 1) 0.91 < 1.00 > 0.99 | vs. | [1:1] |
| 2) 0.70 < 0.81 > 0.78 | vs. | [0.9:1] |
| 3) 0.41 < 0.77 > 0.71 | vs. | [0.7:1] |
| 4) 0.91 > (—) < 0.76 | vs. | [0.7:1] |

Example 3

MM

Spectral data epidermally measured from 3 patients with MM on nucleic acids peaks mean values (965 $cm_{-1}$, 1055 $cm_{-1}$, the most prominent peak in DNA/RNA triad peaks), the intensity ratios and proportional ratios (sum mean DNA/RNA triad peaks vs. 1245 cm-1).

2 MM patterns in 3 patients, based on expressed mean values vs. proportional ratios:

965mean>1055mean<DNA/RNA triad max peak mean

965mean<1055mean<DNA/RNA triad max peak mean

| | | |
|---|---|---|
| 1) 0.19 > 0.14 < 0.27 | vs. | [0.8:1] |
| 2) 0.25 > (—) < 0.35 | vs. | [0.7:1] |
| 3) 0.23 < 0.26 < 0.30 | vs. | [0.8:1] |

2 MM patterns in 3 patients, based on calculated intensity ratios vs. proportional ratios:

$I(965)/I(1245)<I(1055)/I(1245)<I$(DNA/RNA triad max peak)$/I(1245)$ $I(965)/I(1245)>I(1055)/I(1245)<I$(DNA/RNA triad max peak)$/I(1245)$

| | | |
|---|---|---|
| 1) 0.61 < 0.69 < 0.79 | vs. | [0.8:1] |
| 2) 0.63 > 0.47 < 0.90 | vs. | [0.8:1] |
| 3) 0.52 > (—) < 0.73 | vs. | [0.7:1] |

Example 4

Bowen's Disease (Bd)

Spectral data epidermally measured from 4 patients with BCN on nucleic acids peaks mean values (965 $cm_{-1}$, 1055 $cm_{-1}$, the most prominent peak in DNA/RNA triad peaks), the intensity ratios and proportional ratios (sum mean DNA/RNA triad peaks vs. 1245 cm-1).

1 BD pattern in 3 patients, based on mean values:

965mean<1055mean<DNA/RNA triad max peak mean (independent on the grade of activity)

| | | |
|---|---|---|
| 1) (—)  (—)  0.07 | vs. | [0.7:1] |
| 2) 0.09 < 0.15 < 0.18 | vs. | [0.8:1] |
| 3) 0.23 < 0.26 < 0.29 | vs. | [0.9:1] |

1 BD pattern in 3 patients, based on the intensity ratios:

$I(965)/I(1245)<I(1055)/I(1245)<I$(DNA/RNA triad max peak)$/I(1245)$ (independent on the grade of activity)

| | | |
|---|---|---|
| 1) (—)  (—)  0.64 | vs. | [0.7:1] |
| 2) 0.41 < 0.68 < 0.82 | vs. | [0.8:1] |
| 3) 0.70 < 0.79 < 0.88 | vs. | [0.9:1] |

Example 5

Benign Compound Nevus (BCN)

Spectral data epidermally measured from 4 patients with BCN on nucleic acids peaks mean values (965 $cm_{-1}$, 1055 $cm_{-1}$, the most prominent peak in DNA/RNA triad peaks), the intensity ratios and proportional ratios (sum mean DNA/RNA triad peaks vs. 1245 $cm_{-1}$).

1 BCN pattern in 4 patients, based on expressed mean values vs. proportional ratios:

965mean<1055mean<DNA/RNA triad max peak mean

| | | |
|---|---|---|
| 1) 0.15 < 0.22 < 0.23 | vs. | [0.8:1] |
| 2) 0.15 < 0.19 < 0.22 | vs. | [0.7:1] |
| 3) 0.18 < 0.24 < 0.27 | vs. | [0.9:1] |
| 4) 0.12 < 0.17 < 0.19 | vs. | [0.7:1] |

1 BCN pattern in 4 patients, based calculated intensity ratios vs. proportional ratios:

$I(965)/I(1245)<I(1055)/I(1245)<I$(DNA/RNA triad max peak)$/I(1245)$ (independent on the grade of activity)

| | | |
|---|---|---|
| 1) 0.48 < 0.71 < 0.78 | vs. | [0.8:1] |
| 2) 0.47 < 0.59 < 0.72 | vs. | [0.7:1] |

| | | |
|---|---|---|
| 3) 0.56 < 0.75 < 0.84 | vs. | [0.9:1] |
| 4) 0.48 < 0.68 < 0.76 | vs. | [0.7:1] |

Example 6

Healthy Skin (Hs)

HS pattern, based on expressed mean values vs. proportional ratios:

$$965\text{mean} > (\text{no peak expression}) < \text{DNA/RNA triad max peak mean}$$

| | | |
|---|---|---|
| 1) 0.15 > (—) < 0.27 | vs. | [0.5:1] |
| 2) 0.24 > (—) < 0.47 | vs. | [0.5:1] |
| 3) 0.17 > (—) < 0.22 | vs. | [0.7:1] |
| 4) 0.22 > (—) < 0.30 | vs. | [0.7:1] |

HS pattern, based on calculated intensity ratios vs. proportional ratios:

$$I(965)/I(1245) > (\text{no peak expression}) < I(\text{DNA/RNA triad max peak})/I(1245)$$

| | | |
|---|---|---|
| 1) 0.41 > (—) < 0.75 | vs. | [0.5:1] |
| 2) 0.51 > (—) < 1.00 | vs. | [0.5.1] |
| 3) 0.38 > (—) < 0.49 | vs. | [0.7:1] |
| 4) 0.51 > (—) < 0.70 | vs. | [0.7:1] |

Results

Based on the presented Examples 1-5, the activity level of the multiplet at about 1055 cm-1 strongly correlated with the activity level of the most prominent peak expressed in DNA/RNA triad (1071, 1084, 1095 cm-1) in 5 out of 6 patients with BCC, in 3 out of 4 patients with SCC and only in 1 out of 3 patients with MM, as well in all patients with BCN and BD. However, calculated proportional ratios differed for mean values and the intensity ratios between malignant and benign/premalignant, being higher in malignant skin tumours.

Pattern recognition on DNA-RNA and DNA-DNA interactions as $I_{965} < I_{1055} < I_{max\ level\ DNA/RNA\ triad\ peak}$ were the most clearly observed in all 6 patients with BCC, independent on expressed activity levels of all peaks of nucleic acids. The same pattern recognition on DNA-RNA and DNA-DNA interactions were seen in all patients with Bowen's disease and benign compound nevus, again independently on the activity levels expressed by all peaks of nucleic acids.

Pattern recognition on DNA-RNA and DNA-DNA interactions as $I_{965} < I_{1055} > I_{max\ level\ DNA/RNA\ triad\ peak}$ was clearly seen in 3 SCC patients with the highest activity levels of the multiplet at about 1055 cm-1.

In 2 patients with MM pattern recognition on DNA-RNA and DNA-DNA interactions as $I_{965} > I_{1055} < I_{max\ level\ DNA/RNA\ triad\ peak}$ was unique and not seen in any other pathologies, with the lowest activity level of the multiplet.

In 4 healthy subjects pattern recognition on DNA-RNA and DNA-DNA interactions as $I_{965} > (\text{no peak expression}) < I_{max\ level\ DNA/RNA\ triad\ peak}$ was different from all measured above pathologies, with no expression of the multiplet at about 1055 cm-1 in the epidermis.

Intra- and Inter-Molecular Interactions for Proteins

Example 1

| BCC | | |
|---|---|---|
| 1) BCC: 0.5 > 0.4 = 0.4 = 0.4 < 0.7 < 1.0 | vs. | [1:1] |
| 2) BCC: 0.5 > 0.4 = 0.4 = 0.4 < 0.7 < 1.0 | vs. | [1:1] |
| 3) BCC: 0.4 = 0.4 < 0.5 = 0.5 < 0.8 < 1.0 | vs. | [1:1] |
| 4) BCC: 0.2 = 0.2 < 0.3 = 0.3 < 0.7 < 1.0 | vs. | [0.8:1] |
| 5) BCC: 0.2 = 0.2 < 0.3 = 0.3 < 0.8 < 1.0 | vs. | [0.8:1] |
| 6) BCC: 0.2 = 0.2 < 0.3 = 0.3 < 0.7 < 1.0 | vs. | [0.8:1] |

Example 2

| SCC | | |
|---|---|---|
| 1) SCC: 0.7 > 0.6 < 0.7 = 0.7 < 0.9 < 1.0 | vs. | [1:1] |
| 2) SCC: 0.4 = 0.4 = 0.4 = 0.4 < 0.7 < 1.0 | vs. | [0.9:1] |
| 3) SCC: 0.2 = 0.2 < 0.3 = 0.3 < 0.6 < 1.0 | vs. | [0.7:1] |
| 4) SCC: 0.2 = 0.2 = 0.2 = 0.2 < 0.6 < 1.0 | vs. | [0.7:1] |

Example 3

| MM | | |
|---|---|---|
| 1) MM: 0.4 = 0.4 < 0.5 = 0.5 < 0.8 < 1.0 | vs. | [0.8:1] |
| 2) MM: 0.3 = 0.3 < 0.4 = 0.4 < 0.8 < 1.0 | vs. | [0.8:1] |
| 3) MM: 0.5 > 0.4 < 0.5 = 0.5 < 0.8 < 1.0 | vs. | [0.7:1] |

Example 4

| SCC vs. BOWEN'S DISEASE (BD) | | |
|---|---|---|
| 1) SCC: 0.7 > 0.6 < 0.7 = 0.7 < 0.9 < 1.0 | vs. | [1:1] |
| 2) SCC: 0.4 = 0.4 = 0.4 = 0.4 < 0.7 < 1.0 | vs. | [0.9:1] |
| 3) BD: 0.3 < 0.3 < 0.4 = 0.4 < 0.8 < 1.0 | vs. | [0.9:1] |
| 4) BD: 0.2 = 0.2 < 0.3 = 0.3 < 0.7 < 1.0 | vs. | [0.8:1] |
| 5) SCC: 0.2 = 0.2 < 0.3 = 0.3 < 0.6 < 1.0 | vs. | [0.7:1] |
| 6) SCC: 0.2 = 0.2 = 0.2 = 0.2 < 0.6 < 1.0 | vs. | [0.7:1] |
| 7) BD: 0.1 = 0.1 < 0.2 = 0.2 < 0.6 < 1.0 | vs. | [0.7:1] |

Example 6

| MM vs. BENIGN COMPOUND NEVUS (BCN) | | |
|---|---|---|
| 1) BCN: 0.3 > 0.2 < 0.3 < 0.4 < 0.7 < 1.0 | vs. | [0.9:1] |
| 2) BCN: 0.3 > 0.2 < 0.3 < 0.4 < 0.7 < 1.0 | vs. | [0.9:1] |
| 3) BCN: 0.3 > 0.2 < 0.3 = 0.3 < 0.7 < 1.0 | vs. | [0.8:1] |
| 4) BCN: 0.3 > 0.2 < 0.3 = 0.3 < 0.7 < 1.0 | vs. | [0.7:1] |
| 5) BCN: 0.3 = 0.3 < 0.4 = 0.4 < 0.8 < 1.0 | vs. | [0.7:1] |
| 1) MM: 0.4 = 0.4 < 0.5 = 0.5 < 0.8 < 1.0 | vs. | [0.8:1] |
| 2) MM: 0.3 = 0.3 < 0.4 = 0.4 < 0.8 < 1.0 | vs. | [0.8:1] |
| 3) MM: 0.5 > 0.4 < 0.5 = 0.5 < 0.8 < 1.0 | vs. | [0.7:1] |

| ALL MEASURED PATHOLOGIES | | |
|---|---|---|
| 1) BCC: 0.4 = 0.4 = 0.4 < 0.7 < 1.0 | vs. | [1:1] |
| 2) BCC: 0.4 = 0.4 = 0.4 < 0.7 < 1.0 | vs. | [1:1] |
| 3) BCC: 0.4 < 0.5 = 0.5 < 0.8 < 1.0 | vs. | [1:1] |
| 4) SCC: 0.6 < 0.7 = 0.7 < 0.9 < 1.0 | vs. | [1:1] |
| 5) SCC: 0.4 = 0.4 = 0.4 < 0.7 < 1.0 | vs. | [0.9:1] |
| 6) MM: 0.4 < 0.5 = 0.5 < 0.8 < 1.0 | vs. | [0.8:1] |
| 7) MM: 0.3 < 0.4 = 0.4 < 0.8 < 1.0 | vs. | [0.8:1] |
| 8) BCC: 0.2 < 0.3 = 0.3 < 0.7 < 1.0 | vs. | [0.8:1] |
| 9) BCC: 0.2 < 0.3 = 0.3 < 0.7 < 1.0 | vs. | [0.8:1] |
| 10) BCC: 0.2 < 0.3 = 0.3 < 0.7 < 1.0 | vs. | [0.8:1] |
| 11) SCC: 0.2 < 0.3 = 0.3 < 0.6 < 1.0 | vs. | [0.7:1] |
| 12) SCC: 0.2 = 0.2 = 0.2 < 0.6 < 1.0 | vs. | [0.7:1] |
| 13) MM: 0.4 < 0.5 < 0.5 < 0.8 < 1.0 | vs. | [0.7:1] |

Results

Presented data on DNA-protein interactions were mostly expressed between intensities of DNA/RNA triad peaks and non-descriptive proteins at 1310, 1390 and 1450 cm-1, that were in agreement between BCC and SCC, but not in MM.

Protein-protein interactions were similar between the patients, indicating the grade of activity in cells in tissues.

Among the patients with BCC and SCC the levels of non-descriptive proteins generally differed between 0.2 and 0.7. In 3 patients with BCC I (sum mean DNA/RNA triad peaks)/I(1245) was [1:1] and their levels of non-descriptive proteins were stable at the level of 0.4-0.5. Similar levels were observed in 3 patients with MM, but when their I(sum mean DNA/RNA triad peaks)/I(1245) were [0.7:1] and [0.8:1]. In all patients with SCC the levels of non-descriptive proteins were the most sensitive to clearly indicate the activity of I(sum mean DNA/RNA triad peaks)/I(1245). Protein-protein interactions were observed by the correlation between I (amide II)/I(amide I) and mean values of the peaks at about 1310, 1390 and 1450 cm-1. Protein-protein interactions were similar between skin cancers, generally indicating low, medium and high activity levels in cells in tissues.

Bibliography

1. Federman, D. G., Concato, J., Kirsner, R. S., "Screening for skin cancer: absence of evidence", Arch. Dennatol., 145, (2009), 926.
2. DiGiovanni, J., "Multistage carcinogenesis in mouse skin", Pharmacol.
   Ther., 54 (1), (1992), 63-128.
3. Chimento, S. M., Kirsner, R. S., "Understanding the role of c-Jun and Jun B transcription factors in skin cancer development", J. Invest. Dermatol., 131, (2011), 1002.
4. Eikje, N. S., Aizawa, K., Ozaki, Y., "Vibrational spectroscopy for molecular characterization and diagnosis of benign, premalignant and malignant skin tumours", Biotechnology Annual Review, Vol. 11, (2005), 191-226.
5. Eikje, N. S., "Numerical modeling and analytical treatment of IR spectra in the diagnosis of skin cancers", In: SFM 2010: Optical Technologies in Biophysics and Medicine XII (Eds. Tuchin, V. V., Genina, E. A.), Proc SPIE, 7999, (2011), 799909.

The invention claimed is:

1. A method of spectral pattern analysis of nucleic acids and proteins molecules sequentially expressed in benign, premalignant and malignant tumourous skin tissues for characterizing human multistage epidermal carcinogenesis model on a biopsied tissue sample by FTIR microspectroscopy, said method is comprising of:
   (i) assigning in the wavenumber region of 900-1300 $cm^{-1}$ nucleic acids spectral peaks to DNA at 965 $cm^{-1}$, DNA/RNA at 1055 $cm^{-1}$, DNA/RNA triad peak at 1071 $cm^{-1}$, 1084/1085 $cm^{-1}$ and 1095 $cm^{-1}$ to be identified in spectral sequential patterns of nucleic acids corresponding to common and specific expression of the nucleic acids molecules with carcinogenesis of the tissue to be detected in a certain skin tumour type;
   (ii) determining spectral sequential pattern of nucleic acids from assigned sequential appearance of said nucleic acids peaks to be common for benign, premalignant and malignant tumours of skin tissue corresponding to common expression of the nucleic acids molecules with carcinogenesis of the tissue to be detected in a certain skin tumour type;
   (iii) determining spectral sequential pattern of nucleic acids from detected expression levels of said nucleic acids peaks to be specific for benign, premalignant and malignant tumours of skin tissue corresponding to specific expression of the nucleic acids molecules with carcinogenesis of the tissue to be detected in a certain skin tumour type;
   (iv) determining spectral sequential patterns of nucleic acids from calculated intensities of said nucleic acids peaks to be specific for benign, premalignant and malignant tumours of skin tissue corresponding to specific expression of the nucleic acids molecules with carcinogenesis of the tissue to be detected in a certain skin tumour type;
   (v) assigning in the wavenumber region of 1300-1700 $cm^{-1}$ spectral peaks to non-specific proteins at 1310 $cm^{-1}$, 1390 $cm^{-1}$, 1450 $cm^{-1}$ and specific proteins at 1245 $cm^{-1}$, 1540 $cm^{-1}$, 1650 $cm^{-1}$ to be identified in spectral sequential patterns of proteins corresponding to common and specific expression of the proteins molecules with carcinogenesis of the tissue to be detected in a certain skin tumour type;
   (vi) determining spectral sequential patterns of proteins from detected expression levels or calculated intensities of said protein peaks to be specific for benign, premalignant and malignant tumours of skin tissue corresponding to specific expression of the proteins molecules with carcinogenesis of the tissue to be detected in a certain skin tumour type;
   (vii) correlating said spectral sequential patterns of nucleic acids and proteins with calculated proportional ratios of sum mean expression levels of nucleic acids peaks at 1071 $cm^{-1}$, 1084/1085 $cm^{-1}$ and 1095 $cm^{-1}$ to the peak at 1245 $cm^{-1}$ for correspondence with the activity levels of nucleic acids and proteins molecules in benign, premalignant or malignant tumours of skin tissue in association with a certain type; and
   (viii) comparing said spectral sequential patterns of nucleic acids and proteins specific for benign, premalignant and malignant tumours of skin tissue associated with a certain skin tumour type with spectral sequential patterns of nucleic acids and proteins specific for normal skin tissue in association with healthy skin (HS) epidermis.

2. The method of claim 1, wherein determining the spectral sequential patterns of nucleic acids and proteins, specific for benign tumours of skin tissue associated with benign compound nevus (BCN), specific for premalignant tumours of skin tissue associated with Bowen's disease (BD), specific for malignant tumours of skin tissue associated with basal cell carcinoma (BCC), specific for malignant tumours of skin tissue associated with squamous cell carcinoma (SCC), specific for malignant tumours of skin tissue associated with malignant melanoma (MM).

3. The method of claim 1, further comprising spectral pattern analysis of a systemic progression of the grade of neoplastic activity in expressed nucleic acids and proteins molecules in cells in skin tumourous tissues contributing to carcinogenesis from benign to malignant tumourous skin tissue.

4. A method of monitoring the spectral patterns of sequentially expressed nucleic acids and proteins molecules in benign, premalignant and malignant skin tumourous tissues for in vitro diagnosing benign, premalignant and malignant tumours of skin tissue on a biopsied tissue sample in a human, or for in vitro distinguishing between benign, premalignant and malignant tumours of skin tissue on a biopsied tissue sample in a human, or for in vitro monitoring neoplastic activity in benign, premalignant and malignant tumours of skin tissue on a biopsied tissue sample in a human, or for in vitro treatment assessment of benign, premalignant and malignant tumours of skin tissue on a biopsied tissue sample in a human by FTIR microspectroscopy, said method is comprising of the steps (i-viii) according to claim 1.

5. In vitro characterization of the multistage epidermal carcinogenesis directly on a biopsied tissue sample in a human by FTIR microspectroscopy, or in vitro diagnosis of benign, premalignant and malignant tumours of skin tissue in association with a certain type on a biopsied tissue sample in a human by FTIR microspectroscopy, or in vitro monitoring of benign, premalignant and malignant tumours of skin tissue in association with a certain type on a biopsied tissue sample in a human by FTIR microspectroscopy, or in vitro treatment assessment of the treatment of benign, premalignant or malignant tumours of skin tissue in association with a certain type on a biopsied tissue sample in a human by FTIR microspectroscopy, comprising the steps (i-viii) according to claim 1.

6. The method of claim 1, wherein the spectral patterns of sequentially expressed nucleic acids and proteins molecules for benign tumours of skin tissue associated with BCN, is further comprising:
detecting 1 BCN spectral pattern of sequential expression of nucleic acids, based on mean peaks values and intensities as (965 cm$^{-1}$)<1055 cm$^{-1}$)<(1071, 1084/1085, 1095 cm$^{-1}$) versus [0.7:1], or [0.8:1], or [0.9:1], wherein
BCN spectral pattern of nucleic acids as (965 cm$^{-1}$)<(1055 cm$^{-1}$)<(1071, 1084/1085, 1095 cm$^{-1}$) is characterized by mean DNA peak values at 965 cm$^{-1}$ within 0.12-0.18, mean DNA/RNA peak values at 1055 cm$^{-1}$ within 0.17-0.24, mean DNA/RNA triad max peak values at 1071 cm$^{-1}$, 1084/1085 cm$^{-1}$ or 1095 cm$^{-1}$ within 0.19-0.27, mean DNA peak intensities at 965 cm$^{-1}$ within 0.47-0.56, mean DNA/RNA peak intensities at 1055 cm$^{-1}$ within 0.59-0.75, mean DNA/RNA triad max peak intensities at 1071 cm$^{-1}$, 1084/1085 cm$^{-1}$ or 1095 cm$^{-1}$ within 0.72-0.84;
detecting 1 among 3 BCN spectral patterns of sequential expression of proteins, based on mean peaks values and intensities as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) versus [0.7:1], or as (1245 cm$^{-1}$)>(1310 cm$^{-1}$)<(1390 cm$^{-1}$)=(1450 cm$^{-1}$)<(1540 cm$^{-1}$)<(1650 cm$^{-1}$) versus [0.7:1), or [0.8:1), or as (1245 cm$^{-1}$)>(1310 cm$^{-1}$)<(1390 cm$^{-1}$)<(1450 cm$^{-1}$)<(1540 cm$^{-1}$)<(1650 cm$^{-1}$) versus [0.9:1),
wherein BCN spectral pattern of proteins as (1245 cm$^{-1}$)>(1310 cm$^{-1}$)<(1390 cm$^{-1}$)<(1450 cm$^{-1}$)<(1540 cm$^{-1}$)<(1650 cm$^{-1}$) is characterized by mean peaks values and intensities within (0.3)>(0.2)<(0.3)<(04)<(0.7)<(1.0), BCN spectral pattern of proteins as (1245 cm$^{-1}$)>(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within (0.3)>(0.2)<(0.3)=(0.3)<(0.7)<(1.0), BCN spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within (0.3)=(0.3)<(04)=(04)<(0.8)<(1.0); and
calculating characteristic proportional ratio within [0.7:1)-[0.9:1) to be dependent on low grade of activity level of expressed nucleic acids and proteins molecules in spectral patterns of nucleic acids and proteins, corresponding to common and specific expression of the nucleic acids and proteins with carcinogenesis of benign skin tissue to be detected.

7. The method of claim 1, wherein the spectral patterns of sequentially expressed nucleic acids and proteins molecules for premalignant tumours of skin tissue associated with (BD), is further comprising:
detecting 1 among 2 BD spectral patterns of sequential expression of nucleic acids, based on mean peaks values and intensities
as (965 cm$^{-1}$)<(1055 cm$^{-1}$)<(1071, 1084/1085, 1095 cm$^{-1}$) versus [0.81], or [0.9:1], or
as (no peak expression) (no peak expression) (1071, 1084/1085, 1095 cm$^{-1}$) versus [0.7:1],
wherein
BD spectral pattern of nucleic acids as (965 cm$^{-1}$)<(1055 cm$^{-1}$)<(1071, 1084/1085, 1095 cm$^{-1}$) is characterized by
mean DNA peak values at 965 cm$^{-1}$ within 0.09-0.23,
mean DNA/RNA peak values at 1055 cm$^{-1}$ within 0.15-0.26,
mean DNA/RNA triad max peak values at 1071 cm$^{-1}$, 1084/1085 cm$^{-1}$ or 1095 cm$^{-1}$ within 0.18-0.29,
mean DNA peak intensities at 965 cm$^{-1}$ within 0.41-0.70,
mean DNA/RNA peak intensities at 1055 cm$^{-1}$ within 0.68-0.79,
mean DNA/RNA triad max peak intensities at 1071 cm$^{-1}$, 1084/1085 cm$^{-1}$ or 1095 cm$^{-1}$ within 0.82-0.88,
BD spectral pattern of nucleic acids as (no peak expression) (no peak expression) (1071, 1084/1085, 1095 cm$^{-1}$) is characterized by
mean DNA/RNA triad max peak values at 1071 cm$^{-1}$, 1084/1085 cm$^{-1}$ or 1095 cm$^{-1}$ within 0.07,
mean DNA/RNA triad max peak intensities at 1071 cm$^{-1}$, 1084/1085 cm$^{-1}$ or 1095 cm$^{-1}$ within 0.64;
detecting 1 BD spectral pattern of sequential expression of proteins, based on mean peaks values and intensities as 1245 cm$^{-1}$)=(1310 cm$^{-1}$)<11390 cm$^{-1}$)=(1450 cm$^{-1}$)<(1540 cm$^{-1}$)<(1650 cm$^{-1}$) versus [0.7:1], or [0.8:1], or [0.9:1],
wherein
BD spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within
(0.3)=(0.3)<(0.4)=(0.4)<(0.8)<(1.0), or
(0.2)=(0.2)<(0.3)=(0.3)<(0.7)<(1.0), or
(0.1)=(0.1)<(0.2)=(0.2)<(0.6)<(1.0); and calculating characteristic proportional ratio within [0.8:1]-[0.9:1] to be dependent on medium grade of activity level of expressed nucleic acids and proteins molecules in spectral patterns of nucleic acids and proteins, corresponding to common and specific expression of the nucleic acids and proteins with carcinogenesis of pre-cancerous skin tissue to be detected.

8. The method of claim 1, wherein the spectral patterns of sequentially expressed nucleic acids and proteins molecules for malignant tumours of skin tissue associated with MM, is further comprising:

detecting 1 among 3 MM spectral patterns of sequentially expressed nucleic acids, based on mean peaks values and intensities as $(965 \text{ cm}^{-1})<(1055 \text{ cm}^{-1})<(1071, 1084/1085, 1095 \text{ cm}^{-1})$ versus [0.8:1], or as $(965 \text{ cm}^{-1})>(1055 \text{ cm}^{-1})<(1071, 1084/1085, 1095 \text{ cm}^{-1})$ versus [0.8:1], or as $(965 \text{ cm}^{-1})>$(no peak expression)$<(1071, 1084/1085, 1095 \text{ cm}^{-1})$ versus [0.7:1], wherein MM spectral pattern of nucleic acids as $(965 \text{ cm}^{-1})<(1055 \text{ cm}^{-1})<(1071, 1084/1085, 1095 \text{ cm}^{-1})$ is characterized by mean DNA peak values at $965 \text{ cm}^{-1}$ within 0.23, mean DNA/RNA peak values at $1055 \text{ cm}^{-1}$ within 0.26, mean DNA/RNA triad max peak values at $1071 \text{ cm}^{-1}$, $1084/1085 \text{ cm}^{-1}$ or $1095 \text{ cm}^{-1}$ within 0.30, mean DNA peak intensities at $965 \text{ cm}^{-1}$ within 0.61, mean DNA/RNA peak intensities at $1055 \text{ cm}^{-1}$ within 0.69, mean DNA/RNA triad max peak intensities at $1071 \text{ cm}^{-1}$, $1084/1085 \text{ cm}^{-1}$ or $1095 \text{ cm}^{-1}$ within 0.79, MM spectral pattern as $(965 \text{ cm}^{-1})>(1055 \text{ cm}^{-1})<(1071, 1084/1085, 1095 \text{ cm}^{-1})$ is characterized by mean DNA peak values at $965 \text{ cm}^{-1}$ within 0.19, mean DNA/RNA peak values at $1055 \text{ cm}^{-1}$ within 0.14, mean DNA/RNA triad max peak values at $1071 \text{ cm}^{-1}$, $1084/1085 \text{ cm}^{-1}$ or $1095 \text{ cm}^{-1}$ within 0.27, mean DNA peak intensities at 965 cur within 0.63, mean DNA/RNA peak intensities at $1055 \text{ cm}^{-1}$ within 0.47, mean DNA/RNA triad max peak intensities at $1071 \text{ cm}^{-1}$, $1084/1085 \text{ cm}^{-1}$ or $1095 \text{ cm}^{-1}$ within 0.90, MM spectral pattern as $(965 \text{ cm}^{-1})>$(no peak expression)$<(1071, 1084/1085, 1095 \text{ cm}^{-1})$ is characterized by mean DNA peak values at $965 \text{ cm}^{-1}$ within 0.25, mean DNNRNA triad max peak values at $1071 \text{ cm}^{-1}$, $1084/1085 \text{ cm}^{-1}$ or $1095 \text{ cm}^{-1}$ within 0.35, mean DNA peak intensities at $965 \text{ cm}^{-1}$ within 0.52, mean DNA/RNA triad max peak intensities at $1071 \text{ cm}^{-1}$, $1084/1085 \text{ cm}^{-1}$ or $1095 \text{ cm}^{-1}$ within 0.73;

detecting 1 among 2 MM spectral patterns of sequentially expressed proteins, based on mean peaks values and intensities as $(1245 \text{ cm}^{-1})=(1310 \text{ cm}^{-1})<(1390 \text{ cm}^{-1})=(1450 \text{ cm}^{-1})<(1540 \text{ cm}^{-1})<(1650 \text{ cm}^{-1})$ versus (0.8:1), or as $(1245 \text{ cm}^{-1})>(1310 \text{ cm}^{-1})<(1390 \text{ cm}^{-1})=(1450 \text{ cm}^{-1})<(1540 \text{ cm}^{-1})<(1650 \text{ cm}^{-1})$ versus [0.7:1], wherein MM spectral pattern of proteins as $(1245 \text{ cm}^{-1})=(1310 \text{ cm}^{-1})<(1390 \text{ cm}^{-1})=(1450 \text{ cm}^{-1})<(1540 \text{ cm}^{-1})<(1650 \text{ cm}^{-1})$ is characterized by mean peaks values and intensities within $(0.3)=(0.3)<(04)=(04)<(0.8)<(1.0)$, or $(04)=(04)<(0.5)=(0.5)<(0.8)<(1.0)$, MM spectral pattern of proteins as $(1245 \text{ cm}^{-1})>(1310 \text{ cm}^{-1})<(1390 \text{ cm}^{-1})=(1450 \text{ cm}^{-1})<(1540 \text{ cm}^{-1})<(1650 \text{ cm}^{-1})$ is characterized by mean peaks values and intensities within $(0.5)>(04)<(0.5)=(0.5)<(0.8)<(1.0)$; and calculating characteristic proportional ratio within [0.7:1]-[0.8:1] to be dependent on medium grade of activity level of expressed nucleic acids and proteins molecules in sequential patterns of nucleic acids and proteins, corresponding to common and specific expression of the nucleic acids and proteins with carcinogenesis of cancerous skin tissue to be detected.

9. The method of claim 1, wherein the spectral patterns of sequentially expressed nucleic acids and proteins molecules for malignant tumours of skin tissue associated with BCC, is further comprising:

detecting 1 among 3 BCC spectral patterns of sequentially expressed nucleic acids, based on mean peaks values and intensities as $(965 \text{ cm}^{-1})=(1055 \text{ cm}^{-1})<(1071, 1084/1085, 1095 \text{ cm}^{-1})$ versus [0.8:1], or as $(965 \text{ cm}^{-1})<(1055 \text{ cm}^{-1})<(1071, 1084/1085, 1095 \text{ cm}^{-1})$ versus [0.8:1], or [1;1], or as $(965 \text{ cm}^{-1})<(1055 \text{ cm}^{-1})>(1071, 1084/1085, 1095 \text{ cm}^{-1})$ versus [0.8:1], or [1:1], wherein BCC spectral pattern of nucleic acids as $(965 \text{ cm}^{-1})=(1055 \text{ cm}^{-1})<(1071, 1084/1085, 1095 \text{ cm}^{-1})$ is characterized by mean DNA peak values at $965 \text{ cm}^{-1}$ within 0.09, mean DNA/RNA peak values at $1055 \text{ cm}^{-1}$ within 0.09, mean DNA/RNA triad max peak values at $1071 \text{ cm}^{-1}$, $1084/1085 \text{ cm}^{-1}$ or $1095 \text{ cm}^{-1}$ within 0.23, mean DNA peak intensities at $965 \text{ cm}^{-1}$ within 0.45, mean DNA/RNA peak intensities at $1055 \text{ cm}^{-1}$ within 0.45, mean DNA/RNA triad max peak intensities at $1071 \text{ cm}^{-1}$, $1084/1085 \text{ cm}^{-1}$ or $1095 \text{ cm}^{-1}$ within 1.15, BCC spectral pattern of nucleic acids as $(965 \text{ cm}^{-1})<(1055 \text{ cm}^{-1})<(1071, 1084/1085, 1095 \text{ cm}^{-1})$ is characterized by mean DNA peak values at $965 \text{ cm}^{-1}$ within 0.08, or 0.31, or 0.35, mean DNA/RNA peak values at $1055 \text{ cm}^{-1}$ within 0.14, or 0.43, or 0.44, mean DNA/RNA triad max peak values at $1071 \text{ cm}^{-1}$, $1084/1085 \text{ cm}^{-1}$ or $1095 \text{ cm}^{-1}$ within 0.16, or 0.45, or 0.48, mean DNA peak intensities at $965 \text{ cm}^{-1}$ within 0.38, or 0.71, mean DNA/RNA peak intensities at $1055 \text{ cm}^{-1}$ within 0.67, or 0.98, mean DNA/RNA triad max peak intensities at $1071 \text{ cm}^{-1}$, $1084/1085 \text{ cm}^{-1}$ or $1095 \text{ cm}^{-1}$ within 0.76, or 1.09, BCC spectral pattern of nucleic acids as $(965 \text{ cm}^{-1})<(1055 \text{ cm}^{-1})>(1071, 1084/1085, 1095 \text{ cm}^{-1})$ is characterized by mean DNA peak values at $965 \text{ cm}^{-1}$ within 0.11, or 0.35, mean DNA/RNA peak values at $1055 \text{ cm}^{-1}$ within 0.19, or 0.42, mean DNA/RNA triad max peak values at $1071 \text{ cm}^{-1}$ $1084/1085 \text{ cm}^{-1}$ or $1095 \text{ cm}^{-1}$ within 0.18, or 0.40, mean DNA peak intensities at $965 \text{ cm}^{-1}$ within 0.50, or 0.88, mean DNA/RNA peak intensities at $1055 \text{ cm}^{-1}$ within 0.87, or 1.05, mean DNA/RNA triad max peak intensities at 1071 cm$^{-1}$, 1084/1085 cm$^{-1}$ or 1095 cm$^{-1}$ within 0.82, or 1.00;

detecting 1 among 2 BCC spectral patterns of sequentially expressed proteins, based on mean peaks values and intensities as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) versus [0.8:1], or [1:1], or as (1245 cm$^{-1}$)>(1310 cm$^{-1}$)=(1390 cm$^{-1}$)=(1450 cm$^{-1}$)<(1540 cm$^{-1}$)<(1650 cm$^{-1}$) versus [1:1], wherein BCC spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within (0.2)=(0.2)<(03)=(0.3)<(0.7)<(1.0), or
(0.2)=(0.2)<(0.3)=(0.3)<(0.8)<(1.0), or
(04)=(04)<(0.5)=(0.5)<(0.8)<(10), BCC spectral pattern of proteins as (1245 cm$^{-1}$)>(1310 cm$^{-1}$)=(1390 cm$^{-1}$)=(1450 cm$^{-1}$)<(1540 cm$^{-1}$)<(1650 cm$^{-1}$) is characterized by mean peaks values and intensities within (0.5)>(04)=(04)=(04)<(0.8)<(1.0); and calculating characteristic proportional ratio within [0.8:1]-[1:1] to be dependent on low, medium or high grade of activity level of expressed nucleic acids and proteins molecules in sequential patterns of nucleic acids and proteins, corresponding to common and specific expression of the nucleic acids and proteins with carcinogenesis of cancerous skin tissue to be detected.

10. The method of claim 1, wherein the spectral patterns of sequentially expressed nucleic acids and proteins molecules for malignant tumours of skin tissue associated with sec, is further comprising:

detecting 1 among 4 SCC spectral patterns of sequentially expressed nucleic acids, based on mean peaks values and intensities or as 965 cm$^{-1}$)>(no peak expression)<(1071, 1084/1085, 1095 cm$^{-1}$) versus [0.7:1], as 1965 cm$^{-1}$)>(1055 cm$^{-1}$)<(1071, 1084/1085, 1095 cm$^{-1}$) versus [0.7:1], or as (965 cm$^{-1}$)<(1055 cm$^{-1}$)<(1071, 1084/1085, 1095 cm$^{-1}$) versus [0.9:1, or as (965 cm$^{-1}$)<(1055 cm$^{-1}$)>(1071, 1084/1085, 1095 cm$^{-1}$) versus [1:1], wherein SCC spectral pattern of nucleic acids as (965 cm$^{-1}$)>(1055 cm$^{-1}$)<(1071, 1084/1085, 1095 cm$^{-1}$) is characterized by mean DNA peak values at 965 cm$^{-1}$ within 0.19,
mean DNA/RNA peak values at 1055 cm$^{-1}$ within 0.13,
mean DNA/RNA triad max peak values at 1071 cm$^{-1}$, 1084/1085 cm$^{-1}$ or 1095 cm$^{-1}$ within 0.16, SCC spectral pattern of nucleic acids as (965 cm$^{-1}$)<(1055 cm$^{-1}$)<(1071, 1084/1085, 1095 cm$^{-1}$) is characterized by mean DNA peak values at 965 cm$^{-1}$ within 0.26,
mean DNA/RNA peak values at 1055 cm$^{-1}$ within 0.30,
mean DNA/RNA triad max peak values at 1071 cm$^{-1}$, 1084/1085 cm$^{-1}$ or 1095 cm$^{-1}$ within 0.35,
mean DNA peak intensities at 965 cm$^{-1}$ within 0.70,
mean DNA/RNA peak intensities at 1055 cm$^{-1}$ within 0.81,
mean DNA/RNA triad max peak intensities at 1071 cm$^{-1}$, 1084/1085 cm$^{-1}$ or 1095 cm$^{-1}$ within 0.88, SCC spectral pattern of nucleic acids as (965 cm$^{-1}$)<(1055 cm$^{-1}$)>(1071, 1084/1085, 1095 cm$^{-1}$) is characterized by mean DNA peak values at 965 cm$^{-1}$ within 0.60,
mean DNA/RNA peak values at 1055 cm$^{-1}$ within 0.66,
mean DNA/RNA triad max peak values at 1071 cm$^{-1}$, 1084/1085 cm$^{-1}$ or 1095 cm$^{-1}$ within 0.65,
mean DNA peak intensities at 965 cm$^{-1}$ within 0.41, or 0.91,
mean DNA/RNA peak intensities at 1055 cm$^{-1}$ within 0.77, or 1.00,
mean DNA/RNA triad max peak intensities at 1071 cm$^{-1}$, 1084/1085 cm$^{-1}$ or 1095 cm$^{-1}$ within 0.71, or 0.99, SCC spectral pattern of nucleic acids (965 cm$^{-1}$)>(no peak expression)<(1071, 1084/1085, 1095 cm$^{-1}$) is characterized by mean DNA peak values at 965 cm$^{-1}$ within 0.07,
mean DNA/RNA triad max peak values at 1071 cm$^{-1}$, 1084/1085 cm$^{-1}$ or 1095 cm$^{-1}$ within 0.12,
mean DNA peak intensities at 965 cm$^{-1}$ within 0.91,
mean DNA/RNA triad max peak intensities at 1071 cm$^{-1}$, 1084/1085 cm$^{-1}$ or 1095 cm$^{-1}$ within 0.76;

detecting 1 among 3 SCC spectral patterns of sequentially expressed proteins, based on mean peaks values and intensities as (1245 cm$^{-1}$)=(1310 cm$^{-1}$)=(1390 cm$^{-1}$)=(1450 cm$^{-1}$)<(1540 cm$^{-1}$)<(1650 cm$^{-1}$) versus [0.7:1], or [0.9:1], or as (1245 cm$^{-1}$)>(1310 cm$^{-1}$)<(1390 cm$^{-1}$)=(1450 cm$^{-1}$)<(1540 cm$^{-1}$)<(1650 cm$^{-1}$) versus [1:1], or as (1245 cm$^{-1}$)=1310 cm$^{-1}$)<1390 cm$^{-1}$)=(1450 cm$^{-1}$)<(1540 cm$^{-1}$)<(1650 cm$^{-1}$) versus [0.7:1], wherein SCC spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within (0.2)=(0.2)=(0.2)=(0.2)<(0.6)<(1.0), or
(0.4)=(0.4)=(0.4)=(0.4)<(0.7)<(1.0), SCC spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean peaks values and intensities within (0.2)=(0.2)<(0.3)=(0.3)<(0.6)<(1.0), SCC spectral pattern of proteins as (1245 cm$^{-1}$)>(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within (0.7)=(0.6)<(0.7)=(0.7)<(0.9)<(1.0); and calculating characteristic proportional ratio within [0.7:1]-[1:1] to be dependent on low, medium or high grade of activity level of expressed nucleic acids and proteins molecules in sequential patterns of nucleic acids and proteins, corresponding to common and specific expression of the nucleic acids and proteins with carcinogenesis of cancerous skin tissue to be detected.

11. The method of claim 1, wherein the spectral patterns of sequentially expressed nucleic acids and proteins in normal skin tissue associated with HS epidermis, is further comprising:

detecting 1 HS epidermis spectral sequential pattern of nucleic acids molecules with 2 nucleic acids peaks of DNA (965 cm$^{-1}$), the most prominent peak in DNA/RNA triad (1071, 1084/1085, 1095 cm$^{-1}$);

detecting 1 HS epidermis spectral pattern of sequentially expressed nucleic acids peaks with mean values and intensities as (965 cm$^{-1}$)<(DNA/RNA triad max peak) versus [0.5:1] or [0.7:1], wherein
mean DNA peak values at 965 cm$^{-1}$ within 0.15-0.24,
mean DNA/RNA triad max peak values at 1071 cm$^{-1}$, 1084/1085 cm$^{-1}$ or 1095 cm$^{-1}$ within 0.22-0.47,
mean DNA peak intensities at 965 cm$^{-1}$ within 0.38-0.51,
mean DNA/RNA triad max peak intensities at 1071 cm$^{-1}$, 1084/1085 cm$^{-1}$ or 1095 cm$^{-1}$ within 0.49-1.00;
detecting 1 HS epidermis spectral pattern of sequentially expressed proteins peaks with mean values and intensities as (1245 cm$^{-1}$)<(1310 cm$^{-1}$)>(1390 cm$^{-1}$)<(1450 cm$^{-1}$)<(1540 cm$^{-1}$)<(1650 cm$^{-1}$) versus [0.5:1] or [0.7:1],
wherein HS epidermis spectral pattern is characterized by mean peaks values and intensities within (04)<(0.5)>(0.3)<(0.5)<(0.8)<(1.0), or (04)<(0.6)>(04)<(0.5)<(0.8)<(1.0); and
calculating characteristic proportional ratio within [0.5:1]-[0.7:1] to be not dependent on the grade of activity level of expressed nucleic acids and proteins molecules in sequential patterns of nucleic acids and proteins.

12. The method of claim 1, further comprising one of the following:
comparing any received spectral patterns of sequentially expressed nucleic acids and proteins with referenced spectral patterns of sequentially expressed nucleic acids and proteins to be specific for benign, premalignant or malignant skin tumourous tissue with reference to BCC, SCC, MM, BD or BCN, in comparison to normal skin tissue; or
determining in any received spectral patterns of sequentially expressed nucleic acids and proteins which of the differences contribute to the carcinogenesis to be detected between normal and premalignant skin tissue cells, or between normal and malignant skin tissue cells, or between premalignant and malignant skin tissue cells; or
further analysing any received spectral patterns of sequentially expressed nucleic acids and proteins for a systemic progression of the grade of activity of nucleic acids and proteins between normal and benign skin tumourous tissues, characteristic for tumour progression towards benign skin tumourous tissue with reference to BCN; or
further analysing any received spectral patterns of sequentially expressed nucleic acids and proteins for a systemic progression of the grade of activity of nucleic acids and proteins between normal and premalignant skin tumourous tissues, characteristic for tumour progression towards premalignant skin tumourous tissue with reference to BD; or
further analysing any received spectral patterns of sequentially expressed nucleic acids and proteins for a systemic progression of the grade of activity of nucleic acids and proteins between normal and malignant skin tumourous tissues, characteristic for tumour progression towards malignant skin tumourous tissue with reference to MM, or BCC, or SCC; or
further analysing received spectral patterns of sequentially expressed nucleic acids and proteins for a systemic progression of the grade of activity of nucleic acids and proteins within one type of tumour in association with MM to be characteristic for malignant skin tumour progression in the same patient, wherein previously received spectral patterns of sequentially expressed nucleic acids and proteins were characteristic for benign skin tumourous tissue with reference to BCN, in comparison to normal skin tissue; or further analysing received spectral patterns of sequentially expressed nucleic acids and proteins for a systemic progression of the grade of activity of nucleic acids and proteins within one type of tumour with reference to SCC to be characteristic for malignant skin tumour progression in the same patient, wherein previously received spectral patterns of sequentially expressed nucleic acids and proteins were characteristic for premalignant tumourous skin tissue with reference to BD, in comparison to normal skin tissue.

13. The method of claim 1, wherein said expression levels of nucleic acids and proteins peaks are determined in normalized FTIR spectra to amide I at 1650 cm$^{-1}$.

14. The method of claim 1, wherein said benign, premalignant and malignant tumours of skin tissue are selected from the group of BCN, BD, BCC, SCC, MM, is also applicable to other types of benign, premalignant and malignant tumours of skin tissue on a biopsied skin tissue sample in a human.

15. The method of claim 1, which is also applicable for additiDNAI measuring of benign, premalignant and malignant tumourous tissues from other organ epidermal tissues than skin on a biopsied skin tissue sample in a human.

16. A combination group of nucleic acids molecules, specific for benign, premalignant and malignant tumours of skin tissues in association with a certain type, with characteristic intra and inter-molecular expression of DNA and RNA, with characteristic spectral parameters at absorption wave numbers of 965 cm$^{-1}$, 1055 cm$^{-1}$, 1071 cm$^{-1}$, 1084/1085 cm$^{-1}$ and 1095 cm$^{-1}$, by FTIR microspectroscopy, characterized by spectral peaks of nucleic acids to DNA at 965 cm$^{-1}$, DNA/RNA at 1055 cm$^{-1}$, DNA/RNA triad at 1071 cm$^{-1}$, 1084/1085 cm$^{-1}$ and 1095 cm$^{-1}$ corresponding to identity and secondary structures to molecules DNA and RNA, in correlation with their characteristic spectral measurements patterns of the presence, absence and sequentially expressed interacting molecular activity levels by means of nucleic acids peaks values and intensities in the irradiated skin epidermis on a biopsied skin tissue sample of a human, which is one selected from:
(i) a combination group of nucleic acids molecules with characteristic spectral measurements pattern of 3 nucleic acids peaks to DNA 1965 cm$^{-1}$), DNA/RNA (1055 cm$^{-1}$), DNA/RNA triad (1071, 1084/1085, 1095 cm$^{-1}$) by FTIR microspectroscopy, with characteristic interacting molecular activity levels by expressed mean peaks values and intensities in 1 spectral sequential pattern as 1965 cm$^{-1}$)<(1055 cm$^{-1}$)<(DNA/RNA triad max peak), with characteristic mean DNA peak values at 965 cm$^{-1}$ within 0.12-0.18, mean DNA/RNA peak values at 1055 cm$^{-1}$ within 0.17-0.24, mean DNA/RNA triad max peak values at 1071 cm$^{-1}$, 1084/1085 cm$^{-1}$ or 1095 cm$^{-1}$ within 0.19-0.27, mean DNA peak intensities at 965 cm$^{-1}$ within 0.47-0.56, mean DNA/RNA peak intensities at 1055 cm$^{-1}$ within 0.59-0.75, mean DNA/RNA triad max peak intensities at 1071 cm$^{-1}$, 1084/1085 cm$^{-1}$ or 1095 cm$^{-1}$ within 0.72-0.84, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.8:1] or [0.9:1], to be specific for benign tumours of skin tissue in association with BCN on a biopsied tissue sample of a human; or (ii) a combination group of nucleic acids molecules with characteristic spectral measurements pattern of 3 nucleic acids peaks to DMA (965 cm$^{-1}$), DNA/RNA (1055 cm$^{-1}$), DNA/RNA triad (1071, 1084/1085, 1095 cm$^{-1}$) by FTIR microspectroscopy, with characteristic interacting molecular activity levels by expressed mean peaks values and intensities in 1 spectral sequential pattern as (965 cm$^{-1}$)<(1055 cm$^{-1}$)<(1071, 1084/1085, 1095 cm$^{-1}$ max peak), with characteristic mean DNA peak values at 965 cm$^{-1}$ within 0.09-0.23, mean DNA/RNA peak values at 1055 cm$^{-1}$ within 0.15-0.26, mean DNA/RNA triad max peak values at 1071 cm$^{-1}$, 1084/1085 cm$^{-1}$ or 1095 cm$^{-1}$ within 0.18-0.29, mean DNA peak intensities at 965 cm$^{-1}$ within 0.41-0.70, mean DNA/RNA peak intensities at 1055 cm$^{-1}$ within 0.68-0.79, mean DNA/RNA triad max peak intensities at 1071 cm$^{-1}$, 1084/1085 cm$^{-1}$ or 1095 cm$^{-1}$ within 0.82-0.88, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.8:1] or [0.9:1], or 1 nucleic acids peak to DNA/RNA triad (1071, 1084/1085, 1095 cm$^{-1}$) by FTIR microspectroscopy, with characteristic interacting molecular activity levels by expressed mean peaks values and intensities in 1 spectral sequential pattern as (-)<(-)<(DNA/RNA triad max peak), with characteristic mean DNA/RNA triad max peak values at 1071 cm$^{-1}$, 1084/1085 cm$^{-1}$ or 1095 cm$^{-1}$ within 0.07, mean DNA/RNA triad max peak intensities at 1071 cm$^{-1}$, 1084/1085 cm$^{-1}$ or 1095 cm$^{-1}$ within 0.64, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], to be specific for pre-malignant tumours of skin tissue in association with BD on a biopsied tissue sample of a human; or (i) a combination group of nucleic acid molecules with characteristic spectral measurements pattern of 3 nucleic acids peaks to DNA (965 cm$^{-1}$), DNA/RNA (1055 cm$^{-1}$), DNADNA/RNA triad (1071, 1084/1085, 1095 cm$^{-1}$) by FTIR microspectroscopy, with characteristic interacting molecular activity levels by expressed mean peaks values and intensities in 2 spectral sequential patterns as (965 cm$^{-1}$)<(1055 cm$^{-1}$)<(DNA/RNA triad max peak), or as (965 cm$^{-1}$)>(1055 cm$^{-1}$)<(DNA/RNA triad max peak), with characteristic mean DNA peak values at 965 cm$^{-1}$ within 0.19-0.23, mean DNA/RNA peak values at 1055 cm$^{-1}$ within 0.14-0.26, mean DNA/RNA triad max peak values at 1071 cm$^{-1}$, 1084/1085 cm$^{-1}$ or 1095 cm$^{-1}$ within 0.27-0.30, mean DNA peak intensities at 965 cm$^{-1}$ within 0.61-0.63, mean DNA/RNA peak intensities at 1055 cm$^{-1}$ within 0.47-0.69, mean DNA/RNA triad max peak intensities at 1071 cm$^{-1}$, 1084/1085 cm$^{-1}$ or 1095 cm$^{-1}$ within 0.73-0.90, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.8:1], or 2 nucleic acids peaks to DNA (965 cm$^{-1}$), DNA/RNA triad (1071, 1084/1085, 1095 cm$^{-1}$) by FTIR microspectroscopy, with characteristic interacting molecular activity levels by expressed mean peaks values and intensities in 1 spectral sequential pattern as (965 cm$^{-1}$)>(-)<(DNA/RNA triad max peak), with characteristic mean DNA peak values at 965 cm$^{-1}$ within 0.25, mean DNA/RNA triad max peak values at 1071 cm$^{-1}$, 1084/1085 cm$^{-1}$ or 1095 cm$^{-1}$ within 0.35, mean DNA peak intensities at 965 cm$^{-1}$ within 0.52, mean DNA/RNA triad max peak intensities at 1071 cm$^{-1}$, 1084/1085 cm$^{-1}$ or 1095 cm$^{-1}$ within 0.73, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], to be specific for malignant tumours of skin tissue in association with MM on a biopsied tissue sample of a human; or (iv) a combination group of nucleic acid molecules with characteristic spectral measurements pattern of 3 nucleic acids peaks to DNA (965 cm$^{-1}$), DNA/RNA (1055 cm$^{-1}$), DNA/RNA triad (1071, 1084/1085, 1095 cm$^{-1}$) by FTIR microspectroscopy, with characteristic interacting molecular activity levels by expressed mean peaks values and intensities in 3 spectral sequential patterns as (965 cm$^{-1}$)=(1055 cm$^{-1}$)<(DNA/RNA triad max peak), or as (965 cm$^{-1}$)<(1055 cm$^{-1}$)<(DNA/RNA triad max peak), or as (965 cm$^{-1}$)<(1055 cm$^{-1}$)>

(DNA/RNA triad max peak), with characteristic mean DNA peak values at 965 cin within 0.09-0.35, mean DNA/RNA peak values at 1055 cm$^{-1}$ within 0.09-0.44, mean DNA/RNA triad max peak values at 1071 cm$^{-1}$, 1084/1085 cm$^{-1}$ or 1095 cm$^{-1}$ within 0.16-0.48, mean DNA peak intensities at 965 cm$^{-1}$ within 0.38-0.88, mean DNA/RNA peak intensities at 1055 cm$^{-1}$ within 0.45-1.05, mean DNA/RNA triad max peak intensities at 1071 cm$^{-1}$ 1084/1085 cm$^{-1}$ or 1095 cm$^{-1}$ within 0.76-1.15, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.8:1], or [1:1], to be specific for malignant tumours of skin tissue in association with BCC on a biopsied tissue sample of a human; or (v) a combination group of nucleic acids molecules with characteristic spectral measurements pattern of 3 nucleic acids peaks to DMA (965 cm$^{-1}$), DNA/RNA (1055 cm$^{-1}$), DNA/RNA triad (1071, 1084/1085, 1095 cm$^{-1}$) by FTIR microspectroscopy, with characteristic interacting molecular activity levels by expressed mean peaks values and intensities in 3 spectral sequential patterns as (965 cm$^{-1}$)<(1055 cm$^{-1}$)<(DNA/RNA triad max peak), or as (965 cm$^{-1}$)<(1055 cm$^{-1}$)>(DNA/RNA triad max peak), or as 1965 cm$^{-1}$)>(1055 cm$^{-1}$)< (DNA/RNA triad mar peak), with characteristic mean DNA peak values at 965 cm$^{-1}$ within 0.19-0.60, mean DNA/RNA peak values at 1055 cm$^{-1}$ within 0.13-0.66, mean DNA/RNA triad max peak intensities at 1071 cm$^{-1}$, 1084/1085 cm$^{-1}$ or 1095 cm$^{-1}$ within 0.16-0.65, mean DNA peak intensities at 965 cm$^{-1}$ within 0.41-0.91, mean DNA/RNA peak intensities at 1055 cm$^{-1}$ within 0.77-1.00, mean DNA/RNA triad max peak intensities at 1071 cm$^{-1}$, 1084/1085 cm$^{-1}$ or 1095 cm$^{-1}$ within 0.71-0.99, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], or [0.9:1], or [1:1],
or
2 nucleic acids peaks to DNA (965 cm$^{-1}$), DNA/RNA triad (1071, 1084/1085, 1095 cm$^{-1}$) by FTIR microspectroscopy, with characteristic interacting molecular activity levels by expressed mean peaks values and intensities in 3 spectral sequential patterns as (965 cm$^{-1}$)>(-)<(DNA/RNA triad max peak), with characteristic mean DNA peak values at 965 cm$^{-1}$ within 0.07, mean DNA/RNA triad max peak intensities at 1071 cm$^{-1}$, 1084/1085 cm$^{-1}$ or 1095 cm$^{-1}$ within 0.12, mean DNA peak intensities at 965 cm$^{-1}$ within 0.91, mean DNA/RNA triad max peak intensities at 1071 cm$^{-1}$, 1084/1085 cm$^{-1}$ or 1095 cm$^{-1}$ within 0.76, proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], to be specific for malignant tumours of skin tissue in association with SCC on a biopsied tissue sample of a human.

17. A combination group of nucleic acids molecules, specific for benign, premalignant and malignant tumours of skin tissue in association with a certain skin tumour type, with characteristic spectral measurements patterns according to claim 16, selected from a combination group of nucleic acids molecules with characteristic spectral parameters at 965 cm$^{-1}$, 1055 cm$^{-1}$, 1071 cm$^{-1}$, 1084/1085 cm$^{-1}$ or 1095 cm$^{-1}$ FTIR microspectroscopy, for use in characterizing human multistage skin carcinogenesis model on a biopsied tissue sample, or for use in grading neoplastic activity in human benign, premalignant and malignant skin tissue cells on a biopsied tissue sample.

18. A combination group of nucleic acid molecules, specific for benign, premalignant and malignant tumours of skin tissue in association with f certain skin tumour type, with characteristic spectral measurements patterns according to claim 16, selected from a combination group of nucleic acids molecules with characteristic spectral parameters at 965 cm$^{-1}$, 1055 cm$^{-1}$, 1071 cm$^{-1}$, 1084/1085 cm$^{-1}$ or 1095 cm$^{-1}$ by FTIR microspectroscopy, for use in the diagnosis of benign, premalignant and malignant skin tumours on a biopsied tissue sample in a human, or for use in monitoring of benign, premalignant and malignant skin tumours on a biopsied tissue sample in a human, or for use in the treatment assessment of benign, premalignant or malignant skin tumours on a biopsied tissue sample in a human.

19. A combination group of proteins molecules, specific for benign, premalignant and malignant tumours of skin tissue in association with a certain type, with characteristic intra and inter-molecular expression of specific and non-specific proteins, with characteristic spectral parameters at 1245 cm$^{-1}$, 1310 cm$^{-1}$, 1390 cm$^{-1}$, 1450 cm$^{-1}$, 1540 cm$^{-1}$ and 1650 cm$^{-1}$ by FTIR microspectroscopy, characterized by spectral peaks to non-specific proteins at 1310 cm$^{-1}$, 1390 cm$^{-1}$, 1450 cm$^{-1}$ and to specific proteins to amide III at 1245 cm$^{-1}$, amide II
at 1540 cm$^{-1}$, amide I at 1650 cm$^{-1}$ corresponding to identity and secondary structures to molecules of proteins, in correlation with their characteristic spectral measurements patterns of sequentially expressed interacting molecular activity levels by means of proteins peaks values and intensities in the irradiated skin epidermis on a biopsied tissue sample, which is one selected from:

(i) a combination group of proteins molecules with characteristic spectral measurements pattern of specific protein peak to amide III (1245 cm$^{-1}$), non-specific proteins peaks (1310, 1390, 1450 cm$^{-1}$), specific protein peak to amide II (1540 cm$^{-1}$) and specific protein peak to amide I (1650 cm$^{-1}$) by FTIR microspectroscopy, with characteristic interacting molecular activity levels by expressed mean proteins peaks values and intensities in 3 spectral sequential patterns as (1245 cm$^{-1}$)=(1310 cm$^{-1}$)<(1390 cm$^{-1}$)=(1450 cm$^{-1}$)<(1540 cm$^{-1}$)<(1650 cm$^{-1}$), or as (1245 cm$^{-1}$)>(1310 cm$^{-1}$)<(1390 cm$^{-1}$)=(1450 cm$^{-1}$)<(1540 cm$^{-1}$)<(1650 cm$^{-1}$), or as (1245 cm$^{-1}$)>(1310 cm$^{-1}$)<(1390 cm$^{-1}$)<(1450 cm$^{-1}$)<(1540 cm$^{-1}$)<(1650 cm$^{-1}$), with characteristic mean proteins peaks values and intensities at 1245 cm$^{-1}$ within 0.3, at 1310 cm$^{-1}$ within 0.2-0.3, at 1390 cm$^{-1}$ within 0.3-0.4, at 1450 cm$^{-1}$ within 0.3-0.4, at 1540 cm$^{-1}$ within 0.7-0.8, with proportional ratio of calculated sum mean expression levels of nucleic acid peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], or [0.8:1], or [0.9;1], wherein the spectral pattern (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within (0.3)=(0.3)<(0.4)=(0.4)<(0.8)<(1.0) versus[0.7:1], the spectral pattern (1245 cm$^{-1}$)>(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within (03)>(0.2)<(0.3)=(0.3)<(0.7)<(1.0) versus [0.8:1], the spectral pattern (1245 cm$^{-1}$)>(1310 cm$^{-1}$)<(1390 cm$^{-1}$)<(1450 cm$^{-1}$)<(1540 cm$^{-1}$)<(1650 cm$^{-1}$) is characterized by mean proteins peaks values and intensities within (0.3)>(0.2)<(0_3)<(0.4)<(0.7)<(1.0) versus [0.9:1], to be specific for benign tumours of skin tissue in association with BCN on a biopsied sample of a human; or (ii) a combination group of proteins molecules with characteristic spectral measurements pattern of specific protein peak to amide III (1245 cm$^{-1}$), non-specific proteins peaks (1310, 1390, 1450 cm$^{-1}$), specific protein peak to amide II (1540 cm$^{-1}$) and specific protein peak to amide I (1650 cm$^{-1}$) by FTIR microspectroscopy, with characteristic interacting molecular activity levels by expressed mean proteins peaks values and intensities in 1 spectral sequential pattern as (1245 cm$^{-1}$)=(1310 cm$^{-1}$)<(1390 cm$^{-1}$)=(1450 cm$^{-1}$)<(1540 cm$^{-1}$)<(1650 cm$^{-1}$), with characteristic mean proteins peaks values and intensities at 1245 cm$^{-1}$ within 0.1-0.3, at 1310 cm$^{-1}$ within 0.1-0.3, at 1390 cm$^{-1}$ within 0.2-0.4, at 1450 cm$^{-1}$ within 0.2-0.4, at 1540 cm$^{-1}$ within 0.6-0.8, at 1650 cm$^{-1}$ within 1.0, with proportional ratio of calculated sum mean expression levels of nucleic acids peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1, or [0.8:1], or [0.9:1], wherein
the spectral pattern (1245 cm-r)=(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within
(0.1)=(0.1)<(0.2)=(0.2)<(0.6)<(1.0) versus [0.7:1], or
(0.2)=(02)<(0.3) (0.3)<(0.7)<1.0) versus [0.8:1], or
(0.3=0.3<0.4=0.4<0.8<1.0) versus [0.9:1], or
to be specific for premalignant tumours of skin tissue in association with BD on a biopsied sample of a human; or
(iii) a combination group of proteins molecules with characteristic spectral measurements pattern of specific protein peak to amide III (1245 cm$^{-1}$), non-specific proteins peaks (1310, 1390, 1450 cm$^{-1}$), specific protein peak to amide II (1540 cm$^{-1}$) and specific protein peak to
amide I (1650 cm$^{-1}$) by FTIR microspectroscopy, with characteristic interacting molecular activity levels by expressed mean proteins peaks values and intensities in 2 spectral sequential patterns as (1245 cm$^{-1}$)=(1310 cm$^{-1}$)<(1390 cm$^{-1}$)=(1450 cm$^{-1}$)<(1540 cm$^{-1}$)<(1650 cm$^{-1}$), or (1245 cm$^{-1}$)>(1310 cm$^{-1}$)<(1390 cm$^{-1}$)=(1450 cm$^{-1}$)<(1540 cm$^{-1}$)<(1650 cm$^{-1}$), with characteristic mean proteins peaks values and intensities at 1245 cm$^{-1}$ within 0.1-0.3, at 1310 cm$^{-1}$ within 0.1-0.3, at 1390 cm$^{-1}$ within 0.2-0.4, at 1450 cm$^{-1}$ within 0.2-0.4, at 1540 cm$^{-1}$ within 0.6-0.8, at 1650 cm$^{-1}$ within 1.0, with proportional ratio of calculated sum mean expression levels of nucleic acids peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], or [0.8:1], or [09:1],
wherein
the spectral pattern (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within
(0.4)=(0.4)<(0.5)=(0.5)<(0.8)<(1.0) versus [0.8:1], or
(0.3)=(0.3)<(0.4)=(0.4)<(0.8)<(1.0) versus [0.8:1],
the spectral pattern (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by peaks values and intensities within (0.5)>(0.4)<(0.5)=(0.5)<(0.8)<(1.0) versus [0.7:1],
to be specific for malignant tumours of skin tissue in association with MM on a biopsied sample of a human; or
(iv) a combination group of proteins molecules with characteristic spectral measurements pattern of specific protein peak to amide III (1245 cm$^{-1}$), non-specific proteins peaks (1310, 1390, 1450 cm$^{-1}$), specific protein peak to amide II (1540 cm$^{-1}$) and specific protein peak to amide I (1650 cm$^{-1}$) by FTIR microspectroscopy, with characteristic interacting molecular activity levels by expressed mean proteins peaks values and intensities in 2 spectral sequential patterns as (1245 cm$^{-1}$)=(1310 cm$^{-1}$)<(1390 cm$^{-1}$)=(1450 cm$^{-1}$)<(1540 cm$^{-1}$)<(1650 cm$^{-1}$), or (1245 cm$^{-1}$)>(1310 cm$^{-1}$)=(1390 cm$^{-1}$)=(1450 cm$^{-1}$)<(1540 cm$^{-1}$)<(1650 cm$^{-1}$), with characteristic mean proteins peaks values and intensities at 1245 cm$^{-1}$ within 0.2-0.5, at 1310 cm$^{-1}$ within 0.2-0.4, at 1390 cm$^{-1}$ within 0.3-0.5, at 1450 cm$^{-1}$ within 0.3-0.5, at 1540 cm$^{-1}$ within 0.7-0.8, at 1650 cm$^{-1}$ within 1.0, with proportional ratio of calculated stun mean expression levels of nucleic acids peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.8:1], or (1:1],
wherein
the spectral pattern (245 cm$^{-1}$)=(1310 cm$^{-1}$)<(1390 cm$^{-1}$)=(1450 cm$^{-1}$)<(140 cm$^{-1}$)<(1650 cm$^{-1}$) is characterized by mean proteins peaks values and intensities within
(0.2)=(0.2)<(0.3)=(0.3)<(0.7)<(1.0) versus [0.8:1], or
(0.2)=(0.2)<(0.3)=(0.3)<(0.8)<(1.0) versus[0.8:1], or
(0.4)=(0.4)<(0.5)=(0.5)<(0.8)<(1.0) versus[1:1],
the spectral pattern (1245 cm$^{-1}$)>(1310 cm$^{-1}$)=(1390 cm$^{-1}$)=(1450 cm$^{-1}$)<(1540 cm$^{-1}$)<(1650 cm$^{-1}$) is characterized by mean proteins peaks values and intensities within (0.5)>(0.4)=(0.4)=(0.4)<(0.7)<(1.0) versus [1:1],
to be specific for malignant tumours of skin tissue in association with BCC on a biopsied sample of a human; or
(v) a combination group of proteins molecules with characteristic spectral measurements pattern of
specific protein peak to amide III (1245 cm$^{-1}$), non-specific proteins peaks (1310, 1390, 1450 cm$^{-1}$), specific protein peak to amide II (1540 cm$^{-1}$) and specific protein peak to amide I (1650 cm$^{-1}$) by FTIR microspectroscopy, with characteristic interacting molecular activity levels by expressed mean proteins peaks values and intensities in 3 spectral sequential patterns as (1245 cm$^{-1}$)=(1310 cm$^{-1}$)=(1390 cm$^{-1}$)=(1450 cm$^{-1}$)<(1540 cm$^{-1}$)<(1650 cm$^{-1}$), or (1245 cm$^{-1}$)>(1310 cm$^{-1}$)<(1390 cm$^{-1}$)=(1450 cm$^{-1}$)<(1540 cm$^{-1}$)<(1650 cm$^{-1}$), or (1245 cm$^{-1}$)=(1310 cm$^{-1}$)<(1390 cm$^{-1}$)=(1450 cm$^{-1}$)<(1540 cm$^{-1}$)<(1650 cm$^{-1}$), with characteristic mean proteins peaks values and intensities at 1245 cm$^{-1}$ within 0.2-0.7, at 1310 cm$^{-1}$ within 0.2-0.6, at 1390 cm$^{-1}$ within 0.2-0.7, at 1450 cm$^{-1}$ within 0.2-0.7, at 1540 cm$^{-1}$ within 0.6-0.9, at 1650 cm$^{-1}$ within 1.0, with proportional ratio of calculated sum mean expression levels of nucleic acids peaks at 1071 cm$^{-1}$, 1084/1085 cm$^{-1}$ and 1095 cm$^{-1}$ in DNA/RNA triad to DNA/amide III peak value at 1245 cm$^{-1}$ at characteristic range of [0.7:1], or [0.9:1], or [1:1],
wherein
the spectral pattern (1245 cm$^{-1}$)=(1310 cm$^{-1}$)=(1390 cm$^{-1}$)=(1450 cm$^{-1}$)<(1540 cm$^{-1}$)<(1650 cm$^{-1}$) is characterized by mean proteins peaks values and intensities within
(0.2)=(0.2)=(0.2)=(0.2)<(0.6)<(1.0) versus [0.7:1], or
(04)=(04)=(04)=(04)<(0.7)<(1.0) versus [0.9:1],
the spectral pattern (1245 cm$^{-1}$)>(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within
(0.7)>(0.6)<(0.7)=(0.7)<(0.9)<(1.0) versus [1:1], or
the spectral pattern of proteins as (1245 cm$^{-1}$)=(1310 cm$^{-1}$)<(1390 cm$^{-1}$)=(1450 cm$^{-1}$)<(1540 cm$^{-1}$)<(1650 cm$^{-1}$) is characterized by mean proteins peaks values and intensities within
(02)=(02)<(03)=(03)<(0.6)<(1.0) versus [0.7:1],
to be specific for malignant tumours of skin tissue in association with SCC on a biopsied sample of a human.

20. A combination group of proteins molecules, specific for benign, premalignant and malignant tumours of skin tissue in association with a certain skin tumour type, with characteristic spectral measurements patterns according to claim 19, selected from a combination group of proteins molecules with characteristic spectral parameters at 1245

$cm^{-1}$, 1310 $cm^{-1}$, 1390 $cm^{-1}$, 1450 $cm^{-1}$, 1540 $cm^{-1}$ and 1650 $cm^{-1}$ by FTIR microspectroscopy, for use in establishing human multistage skin carcinogenesis model on a biopsied tissue sample, or for use in grading neoplastic activity in human benign, premalignant and malignant skin tissue cells on a biopsied tissue sample.

21. A combination group of proteins molecules, specific for benign, premalignant and malignant tumours of skin tissue in association with a certain skin tumour type, with characteristic spectral measurements patterns according to claim 19, selected from a combination group of proteins molecules with characteristic spectral parameters at 1245 $cm^{-1}$, 1310 $cm^{-1}$, 1390 $cm^{-1}$, 1450 $cm^{-1}$, 1540 $cm^{-1}$ and 1650 $cm^{-1}$ by FTIR microspectroscopy, for use in the diagnosis of benign, premalignant and malignant skin tumours in association with a certain type on a biopsied tissue sample in a human or for use in monitoring of benign, premalignant and malignant skin tumours in association with a certain type on a biopsied tissue sample in a human, or for use in treatment assessment of benign, premalignant or malignant skin tumours in association with a certain type on a biopsied tissue sample in a human.

\* \* \* \* \*